(12) United States Patent
Nisch et al.

(10) Patent No.: US 6,218,663 B1
(45) Date of Patent: Apr. 17, 2001

(54) PROCESS AND DEVICE FOR ION THINNING IN A HIGH RESOLUTION TRANSMISSION ELECTRON MICROSCOPE

(75) Inventors: Wilfried Nisch, Tübingen; Peter Gnauck, Reutlingen, both of (DE)

(73) Assignee: NMI Naturwissenschaftliches und Medizinisches (DE)

( * ) Notice: Subject to any disclaimer, the term of this patent is extended or adjusted under 35 U.S.C. 154(b) by 0 days.

(21) Appl. No.: 09/011,594

(22) PCT Filed: Jul. 24, 1996

(86) PCT No.: PCT/DE96/01408

§ 371 Date: Jan. 28, 1998

§ 102(e) Date: Jan. 28, 1998

(87) PCT Pub. No.: WO97/05644

PCT Pub. Date: Feb. 13, 1997

(30) Foreign Application Priority Data

Jul. 25, 1995 (DE) ............................................. 195 27 059

(51) Int. Cl.[7] ................................................. H01J 37/30
(52) U.S. Cl. ........................... 250/309; 250/307; 250/311
(58) Field of Search .................................. 250/309, 311, 250/307, 452.21, 397

(56) References Cited

U.S. PATENT DOCUMENTS

| | | | |
|---|---|---|---|
| 4,128,765 | 12/1978 | Franks | 250/442.11 |
| 5,023,453 | * 6/1991 | Adahi et al. | 250/309 |
| 5,331,161 | * 7/1994 | Ohdomari et al. | 250/309 |
| 5,443,684 | * 8/1995 | Eckeart et al. | 156/626.1 |
| 5,525,806 | * 6/1996 | Iwasaki et al. | 250/311 |
| 5,656,811 | * 8/1997 | Itoh et al. | 250/309 |
| 5,852,297 | * 12/1998 | Ishitani et al. | 250/492.21 |

FOREIGN PATENT DOCUMENTS

| | | |
|---|---|---|
| 2243616 | of 0000 | (DE) . |
| 29507225 | of 0000 | (DE) . |
| 6231719 | of 0000 | (JP) . |
| 7092062 | of 0000 | (JP) . |

OTHER PUBLICATIONS

A. Benninghoven et al, Secondary Ion Mass Spectrometry, John Wiley and Sons, 1987, Chapter 4.1.9.

* cited by examiner

*Primary Examiner*—Bruce C. Anderson
(74) *Attorney, Agent, or Firm*—Chadbourne & Parke LLP

(57) ABSTRACT

The invention concerns an "in situ" ion-etching device for local thinning of a sample in a transmission electron microscope (1) with simultaneous electron microscopic observation. Towards this end, an ion beam device (2) is arranged in such a way that the finest possible ion probe is produced at the sample location and can be scanned over the sample surface. The ion beam (16) and sample (10) thereby enclose the flattest possible angle. To compensate for the magnetic field of the objective lens (5), the ion beam (16) is defected along a curved path onto the sample (10). In a preferred embodiment, an electrostatic cylinder capacitor sector field effects double focusing. The ion probe can be positioned, via the scanned ion image, onto a selected region of the sample by the secondary electrons (22) released from the sample (10). The sample location can be observed during the ion thinning process in electron transmission or electron diffraction. It is thereby possible to carry out target preparations under high-resolution observing conditions and to eliminate contaminant or reactive layers.

14 Claims, 8 Drawing Sheets

PROCESS AND DEVICE FOR ION THINNING IN A HIGH RESOLUTION TRANSMISSION ELECTRON MICROSCOPE

BACKGROUND OF THE INVENTION

The invention concerns a method and associated device for ion thinning of a sample in a sample region of a transmission electron microscope having an objective lens and comprising an ion source for the production of an ion beam, an ion lens, a secondary electron detector for the production of an ion scan secondary electron image of the sample surface with the assistance of the secondary electrons released during scanned ion irradiation and for the positioning of the ion beam, via the ion scan secondary electron image, onto a particular location of the sample.

Samples are prepared for high resolution transmission electron microscopy by being pre-thinned in a conventional manner, using mechanical or chemical procedures, to an initial thickness of ca. 10 μm. The samples are subsequently ion thinned through bombardment with an ion beam with the ion beam at as flat an angle as possible with respect to the sample surface until a small hole of approximately 100–200 μm in diameter is produced in the middle of the sample. The sample is then sufficiently thin within a wedge-shaped region in the edge portion of the hole and is transparent for fast electrons in excess of 100 keV.

For high resolution transmission electron microscopy the amount of inelastic scattering of the electrons in the sample is low, so that it is necessary for the sample to be sufficiently thin. A high lateral resolution of approximately 1.5 nm, corresponding to an electromicroscopic enlargement of 100,000, can be achieved beginning with a thickness of approximately 100 nm. In highest resolution transmission electron microscopy with which lateral resolutions of up to 0.15 nm are achieved, corresponding to magnification factors of 1 million, it is necessary for the sample to be thinned to a thickness of less than 10 nm. In addition to high resolution electron microscopy, very thin object locations free from reactive layers, contamination layers and amorphous layers damaged by ion thinning, are also required in electron holography.

The usual ion thinning procedures utilized for sample preparation in transmission electron microscopy work in a substantially "blind" manner. Whether or not a desired object feature is properly enhanced with good quality through preparation is more or less a question of luck. Devices of prior art have therefore been proposed with which a sample in a transmission electron microscope sample holder can be thinned in an external etching device under simultaneous observation.

The publication Gatan Inc., 6678 Owens Drive, Pleasanton, Calif. 94566 USA product specification "Precision Ion Milling System" (PIMS), model 645, June 1987, has proposed imaging of the released secondary electrons for this purpose. The publications H. Bach, Bosch Technische Berichte 1, 1964, 10–13 and F. Nagata et al., Proc. 41 st. Confer. JSEM. 1985, 133, have proposed observing the sample for ion thinning in the first imaging plane of a transmission electron microscope in transmission mode.

These conventional etching devices have the disadvantage that the resolution which can be achieved for evaluation of the sample quality is insufficient and that, after ion thinning, it is necessary to introduce the sample along with the sample holder into the field of the objective lens for high resolution observation of the sample. The thin sample thereby reacts with air and with residual gas causing undesirable reaction and contamination layers.

It is furthermore disadvantageous that a plurality of transfers are normally necessary between high resolution observation and additional thinning in order to achieve the desired layer thickness. It is thereby not only difficult to once more locate the object position for renewed observation, which can be extremely difficult for high lateral resolution, but the high resolution transmission electron microscopic observation also causes disturbing contaminating layers due to the high energy electron irradiation, in particular from hydrocarbons. It can therefore be necessary to prepare a new sample location through renewed thinning at another location.

Another problem which occurs during high resolution transmission electron microscopy is associated with the fact that the objective lens cannot be arbitrarily switched-on and off. The objective lens produces the magnetic field necessary for high resolution at the location of the sample of ca. 1 to 2 T and effects a constant magnification of 100 to 200. When switching-on the objective lens, drifts occur due to various influences such as current stability, heat expansion and heat equilibration effects as well as other causes which require a time duration of two hours or longer to damp to a level sufficiently stable for observation. It is therefore not possible to quickly change from high resolution observation with switched-on objective lens having a magnification of approximately 1,000,000 to low, long focal length magnification with the objective lens switched-off with, if appropriate, switching-on a mini or intermediate lens producing no magnetic field in the objective plane having ca. 10,000-fold magnification. On the other hand, due to the very limited amount of space particularly in the region of the objective lens, it is not possible to move a sample in the vacuum of the transmission electron microscope out of the first imaging plane position into the objective plane. In order to do this, the sample must be passed through a vacuum lock.

DE 29507225 U1 proposes an ion beam preparation device for electron microscopy which facilitates ion thinning during simultaneous electron microscopic observation. A high resolution observation is however not possible with the configuration proposed therein, since no magnetic field is present at the location of the sample due to the lack of an objective lens located therein. The electron energy is also low. The sample is not disposed in the sample region of the objective lens of a transmission electron microscope.

JP-(A) 6-231719 proposes a preparation method for the preparation of cuts in semiconductors with which a sample location having a passive protective layer of ca. 100 nm thickness is thinned in the objective plane of the objective lens of a transmission electron microscope using a fast-ion-beam-ion source of 30 keV. The high energy of the ions substantially reduces problems with regard to working separations but causes radiation damage and the large amount of material removal leads to deposits on the lenses and therefore to imaging distortions. Nor is it possible with the apparatus proposed in this publication to thin the sample under high resolution conditions, i.e. with magnifications in excess of 10,000 or 100,000, since the ion beam is not incident on the sample when the objective lens is switchedon. The publication therefore proposes switching back and forth between ion thinning and higher resolution which is associated with the above mentioned disadvantages.

Those of average skill in the art have believed that it is necessary to carry out ion thinning with the objective lens switched-off to allow the ion beam to be incident on the sample location. The disadvantages associated therewith were accepted up to this point in time.

SUMMARY OF THE INVENTION

Departing from this prior art it is the underlying purpose of the invention to improve the preparation techniques for transmission electron microscopy in such a manner that the sample can be thinned "in situ" under simultaneous high resolution transmission electromicroscopic observation in the objective plane of the transmission electron microscope to prevent renewed reformation of reactive layers in air, to shorten the duration of the experimental times, and to be able to thin particular sample locations or sample regions to a defined monitored extent.

This purpose is achieved in accordance with the invention with an ion-etching device for ion thinning of a sample in a sample region of a transmission electron microscope with an objective lens, including an ion source for the production of an ion beam and an ion lens, a secondary electron detector for the production of an ion scanning secondary electron image of the sample surface with the assistance of the secondary electrons released during scanned ion irradiation and for the positioning the ion beam, via the ion scanned secondary electron image, onto a particular sample location. The invention is characterized in that the incidence direction of the ion beam into the magnetic sector field of the objective lens through which the ions pass is chosen in such a fashion that the magnetic sector field passed through by the ions deflects the ions along a curved path onto the sample so that, with the objective lens switched-on, the sample location can be simultaneously observed along with the ion scanned secondary electron image and with the electron beam of the transmission electron microscope in transmission mode.

Within the framework of the present invention, it has surprisingly been found th at the extremely difficult requirements associated with transmission electron microscopes due to the high magnetic field and the very limited amount of space caused by the objective lens can be satisfied by compensating for the influence of the magnetic field of the switched-on objective lens on the ion beam by introducing the ion beam to the sample location under the influence of the magnetic field along an ion optical path which is not a straight line rather curved without, as had been thought necessary up to this point in time, having to switch-off the objective lens for ion thinning under simultaneous transmission electron microscopic observation. Towards this end, the ion beam device is disposed in a mechanically decentralized manner, that means by a skewed introduction of the ion beam, or the ion beam passes special deflection plates effecting a slanted introduction or deflection of the beam. In accordance with the invention, the ion beam is precisely deflected or curved to once more be incident on the sample under the influence of the magnetic field perpendicular to the objective plane.

The invention achieves goals which those of average skill in the art have been striving to achieve for some time. The invention allows, for the first time and under high resolution conditions i.e. with magnification factors in excess of 10,000 to ca. 1,000,000 corresponding to lateral resolutions of 1.5 nm to approximately 0.15 nm, for the local thinning of a sample location or a sample region "in situ" to thereby prepare desired sample locations and sample thickness without having to introduce the sample into an external etching device or into the first imaging plane of the transmission electron microscope or without requiring a long lead time for the achievement of a stable operation condition of the objective lens. The controlled ion thinning furthermore reduces soiling problems in the transmission electron microscope caused by preparation.

In accordance with an additional advantageous feature, an ion focus on a sample location can be adjusted by means of the ion lens. The ion focus advantageously has a diameter between 0.5 and 100 $\mu$m, preferentially between 0.5 and 20 $\mu$m and particularly preferentially between 1 and 10 $\mu$m. It thereby corresponds to the lateral dimensions of an observed object location so that a local ion thinning can be carried out which is not spreadout over a certain area. Deposits on the objective lens and in other regions of the transmission electron microscope with the associated soiling problems are thereby substantially reduced.

In accordance with prior art, an ion focus of approximately 0.1 $\mu$m diameter can be achieved with ion sources operating under optimal conditions. This is however not possible in accordance with present conventional techniques for transmission electron microscopy due to the difficult conditions caused by the dimensions and the magnetic field of the objective lens. In order to achieve as small a beam diameter as possible at the sample location it is, however, advantageous for ion optical reasons to maintain as small a working separation between the ion beam device and the sample location as possible, preferentially less than 5 cm, since the imaging errors of the ion lens increase with increasing focal length.

In accordance with another advantageous feature, the ion energy is less than 5 keV, preferentially less than 3 keV in order to reduce radiation damage in the sample. Although focusing is thereby more difficult than at higher ion energies, it has turned out that even low energies can be utilized within the framework of the invention. The ion source can, for example, be a gas ion source using cold ionization, for example, a saddle field ion source or have electron impact ionization, for example, a hot cathode ion source which can be operated with rare gases (for example Ar or He) or with reactive gases (for example $O_2$, $N_2$ or Freon). Gas-field ion sources (He, $H_2$) or liquid metal-field ion sources (for example Ga or In), have turned out to be particularly advantageous for achieving as small a beam diameter as possible at the sample location, since same have lower energy and directional defocusing.

The curved ion optical path of the ion beam in accordance with the invention while passing through the magnetic sector field of the switched-on objective lens results in deflection of the ions onto the desired sample location. By taking into consideration the deflection of the ions in the magnetic field and by adjusting an appropriate input direction, for example with slanted configuration of the ion beam source or by means of a curved pair (for example cylindrical capacitor) of electrostatic deflectors, it is possible, in most cases, to achieve sufficient focusing of the ion beam onto the sample location even when the objective lens is switched-on, particularly when utilizing liquid-metal ion sources. A small amount of fanning-out and defocusing of the ion beam caused by the energy and directional defocusing of the ion beam, which is tolerable in many cases, can not thereby be completely avoided, even in the event of a homogenous magnetic field.

In order to further improve the focusing, a preferred feature proposes providing deflection plates of an electrostatic cylindrical capacitor sector field configured in such a fashion that, in combination with the magnetic sector field of the objective lens through which the ions pass, double focusing of the ions with respect to energy and directional dispersion is effected. The energy and directional dispersion of the ions in the magnetic field can be compensated for by the cylindrical capacitor sector field to facilitate sharper focusing.

Double focusing with respect to energy as well as initial direction of the ions is known in the art of mass spectrometers. For details one is referred to the respective literature, e.g. A. Benninghoven et al., Secondary Ion Mass Spectrometry, John Wiley & sons (1987) chapter 4.1.9. The double focusing provides a bunching of the ions entering into the magnetic field in parallel planes. Both directional focusing as well as velocity focusing are thereby achieved. Particles of the same mass, whose velocities or directions deviate somewhat with respect to each other, are approximately brought together at a point or line. Also within the context of the invention with transmission electron microscopes, the lines can be focused to a point through additional electron optical components, for example stigmators.

In accordance with the invention, transmission electron microscope samples can be locally ion thinned "in situ" directly in the transmission electron microscope under high resolution observation. In this manner, target preparations can be carried out in a monitored fashion and contamination and reactive layers can be directly removed in the microscope vacuum.

Additional advantageous features and characteristics can be derived from the following embodiments of the invention which are described and explained with regard to the schematic representation of the drawings.

BRIEF DESCRIPTION OF THE DRAWINGS

FIG. 4 shows a first path in accordance with the invention of an ion beam with the objective lens switched-on.

DETAILED DESCRIPTION OF THE INVENTION

Figure 1:
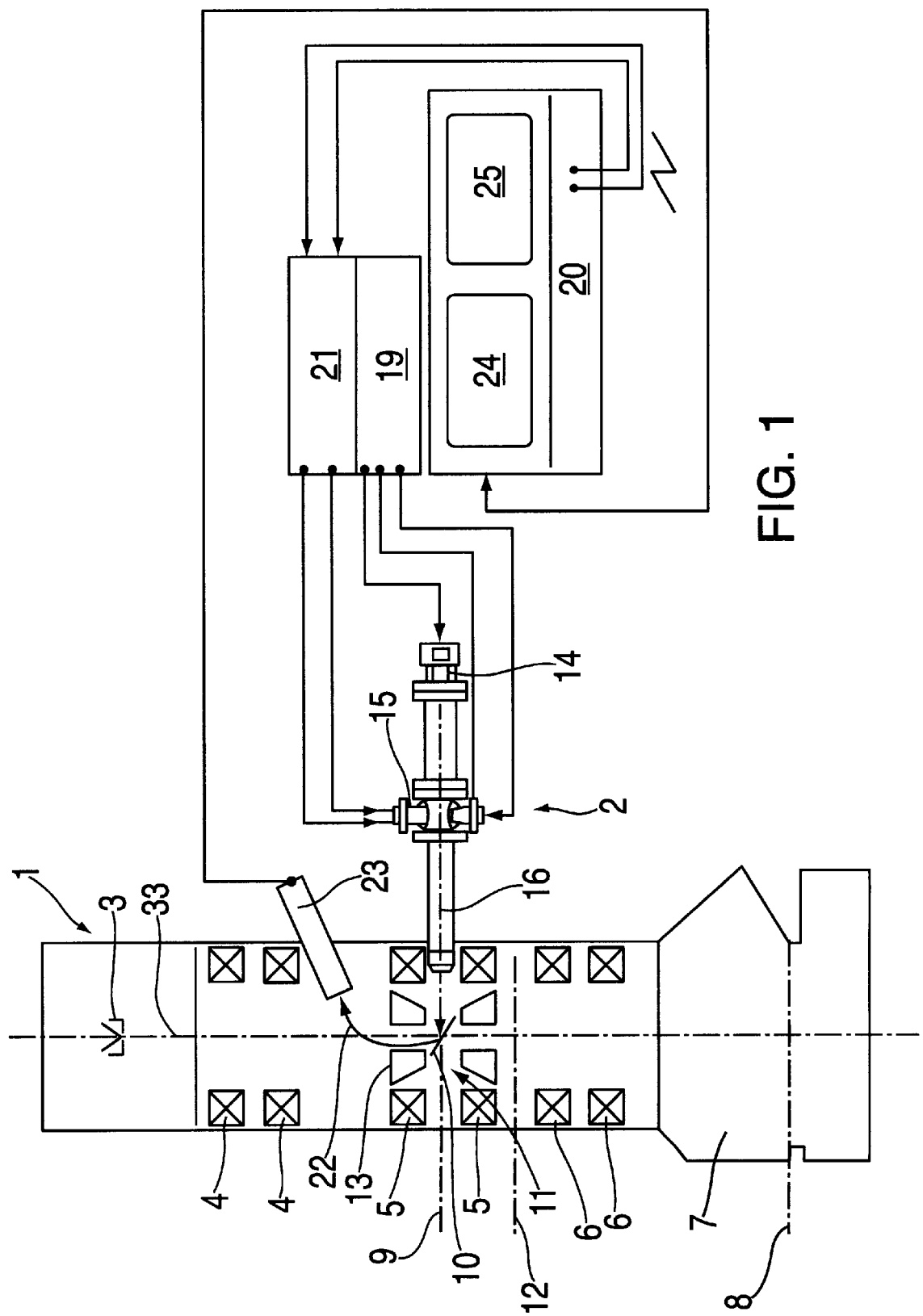
FIG. 1 show a transmission electron microscope according to the invention.

FIG. 1 shows a transmission electron microscope 1 having an ion-etching device in accordance with the invention and electronic control of the ion beam device 2. The electron optical column of a transmission electron microscope 1 typically consists essentially of an electron beam source 3, the condenser lenses 4, the objective lens 5, the projection lenses 6 and the observation region 7 with a fluorescent screen in the observation plane 8. The electron beam generator 3 produces electrons having energies in excess of 100 keV and normally of 200 keV. FIG. 1 also shows the objective plane 9, in which the sample 10 is located in sample region 11 and the first imaging plane 12 in which the electron image of the objective lens 5 is located. The sample 10 is located in the objective plane 9 between the pole pieces 13 of the objective lens 5 during imaging.

The ion beam device 2 includes an ion source 14 and an ion lens 15 for the production of an ion beam 16. The ion beam device is disposed in the objective plane 9 at the same level as the sample 10 during imaging. The ion beam device is connected to the microscope column vacuum with a special vacuum flange in such a fashion that a pressure step is formed at the sample location relative to the vacuum region in the objective lens 5 via of a collimator 17 built into the ion beam device 2. The vacuum region in the ion beam device 2 between the collimator 17 and an additional collimator 18 can be evacuated via a second pump, independent of the objective or sample region 11 of the transmission electron microscope 1. This differential pumping system prevents the vacuum of the ion beam device 2 from influencing the sample region 10 and vice versa.

The electronic control of the ion beam device 2 includes a voltage supply 19 for the ion source 14 and for the ion lens 15, a scan generator 20 and a deflection amplifier 21. The ion beam 16 can be scanned over the sample 10 using the scan generator 20. A raster scanning ion image can be displayed using the secondary electron detector 23 on the scanning ion image monitor 24 via the secondary electrons 22 thereby released from the sample 10 (the arrow illustrates the path of the secondary electrons 22). The scanning electron image produced by the electron beam of the transmission electron microscope 1 in reflection or transmission can simultaneously be observed on the scanning electron image monitor 25. In this fashion, the ion beam 16 can be easily aligned onto a particular sample location 26 or a particular sample region of the sample 10 at which ion thinning should be effected using the ion beam 16. The sample location 26 can be observed in the observation plane 8 with the transmission electron microscope 1 during simultaneous ion thinning.

The ion beam 16 can be guided by means of control deflection plates in a scan-like fashion over the sample surface. The transmission electron microscope 1 can preferentially be a scanning transmission electron microscope, wherein the deflection of the ion beam 16 is advantageously controllable by the scanning unit of the scanning transmission electron microscope and the secondary electron image can be recorded by means of the secondary electron detector 23 of the scanning transmission electron microscope.

Figure 2:
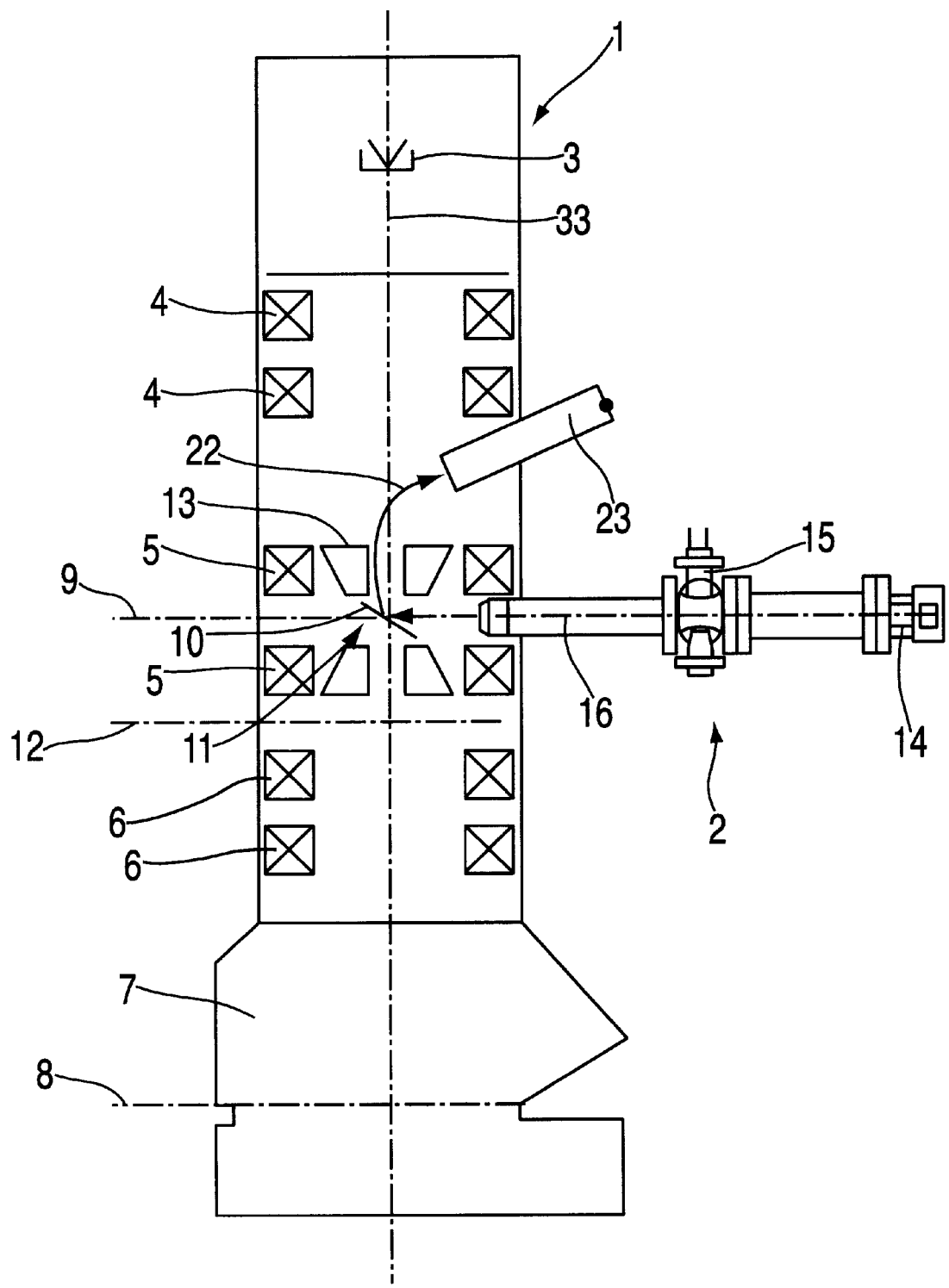
FIG. 2 shows a detail of FIG. 1.

FIG. 2 shows the transmission electron microscope 1 of FIG. 1 and the ion beam device 2 without the electronic control. A long focal length mini lens (not shown) may be disposed in the vicinity of the projection lens 6 to effect a magnification of ca. 10,000 when the objective lens 5 is switched-off. One recognizes the very limited amount of space in the vicinity of the pole pieces 13 of the objective lens 5 which makes the holding of the sample 10, the introduction of the ion beam 16, as well as the detection of the secondary electrons 22 using the secondary electron detector 23 difficult and which prevents displacement of the sample 10 within the transmission electron microscope 1. into the first imaging plane 12.

Figure 3:
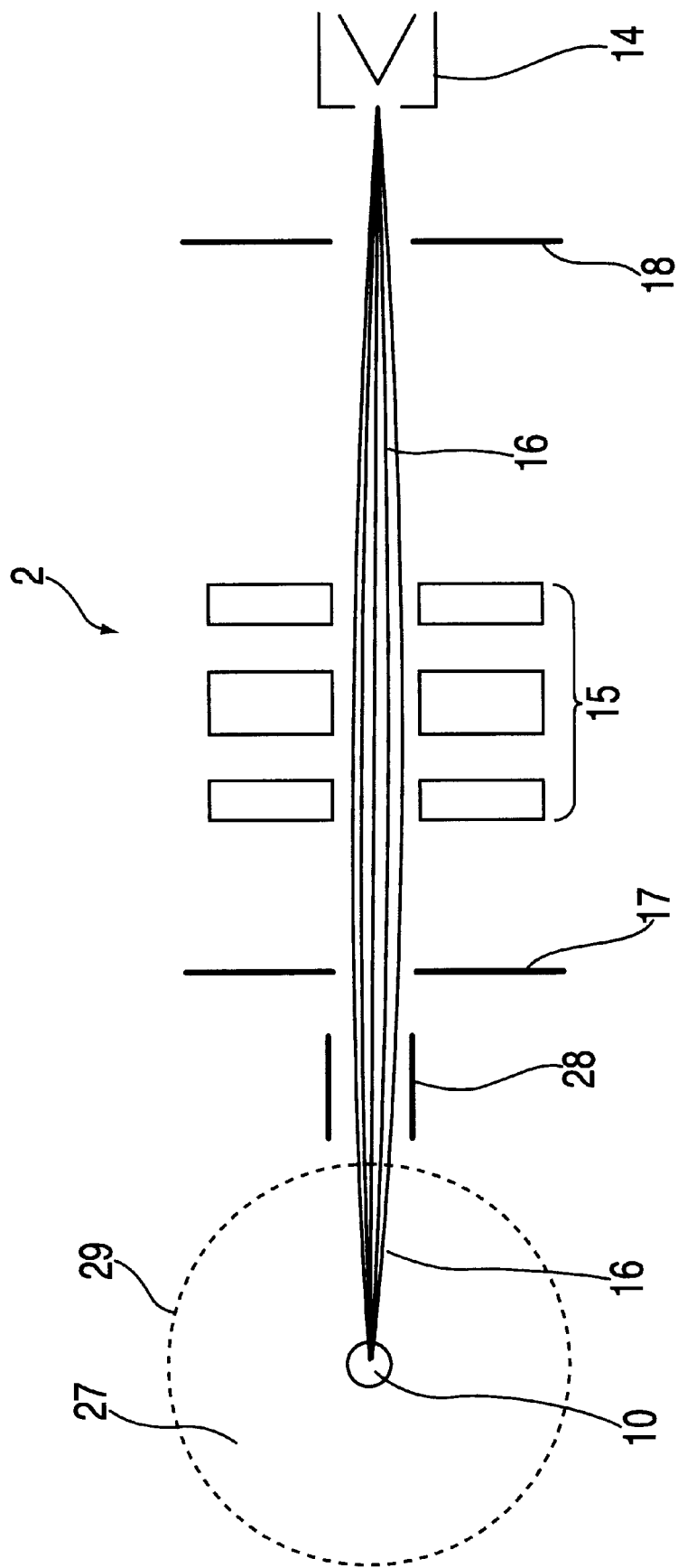
FIG. 3 shows a schematic sketch of an ion beam path with the objective lens switched-off.

FIG. 3 shows the path of the ion beam 16 when the magnetic field 27 of objective lens 5 is switched-off. The ion lens 15 focuses the ion beam 16 onto the sample 10. The collimators 17, 18 form a pressure step to separate the vacuum region of the ion beam device 2 from sample region 11. The ion beam 16 can be scanned over the sample 10 in the objective plane 9 and at right angles thereto via the deflection plates 28 and steered onto a particular desired sample location 26. Only small magnifications with reduced resolution are thereby possible through magnification via the projective lens 6 or another auxiliary lens.

When the magnetic field 27 of the objective lens 5 is switched-on, the ion beam 16 is also deflected beginning at the pole piece edge 29 of the objective lens 5, by the strong magnetic field 27 of the objective lens 5 and is no longer incident on the sample 10. This cannot be compensated for by an axis-parallel deflection plate 28. Ion-etching is thereby only possible in the conventional configuration shown when the objective lens 5 is switched-off. If the sample 10 is to be observed with high resolution and magnification, one must switch back and forth between ion-etching and transmission electronmicroscopic observation, wherein the above mentioned disadvantages with regard to reactions on the sample 10 and the necessary experimental time must be accepted.

Figure 4:
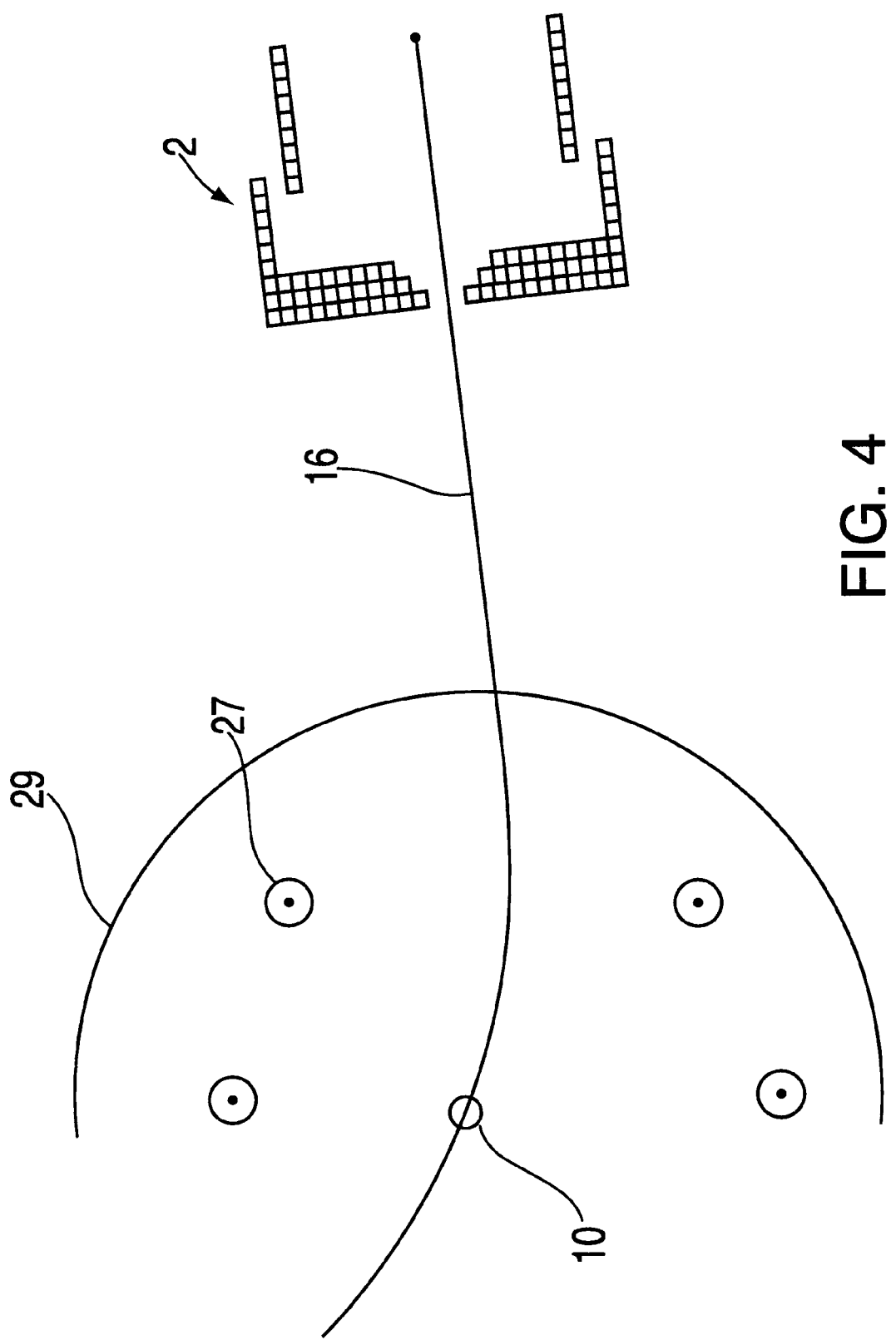

FIG. 4 shows a first configuration in accordance with the invention with which the incident direction of the ion beam 16 into the magnetic field 27 though which the ions pass is chosen in such a fashion as to deflect the ion along a curved path leading, when the objective lens 5 is switchedon, onto the sample 10 and in particular onto a desired location of the sample 26. The ion beam device 2 is shown in a schematic fashion. The ion beam 16 is not introduced radially into the magnetic field 27, rather at a particular incident angle. Towards this end, the ion beam device 2 is displaced sideward or rotated.

Figure 5:
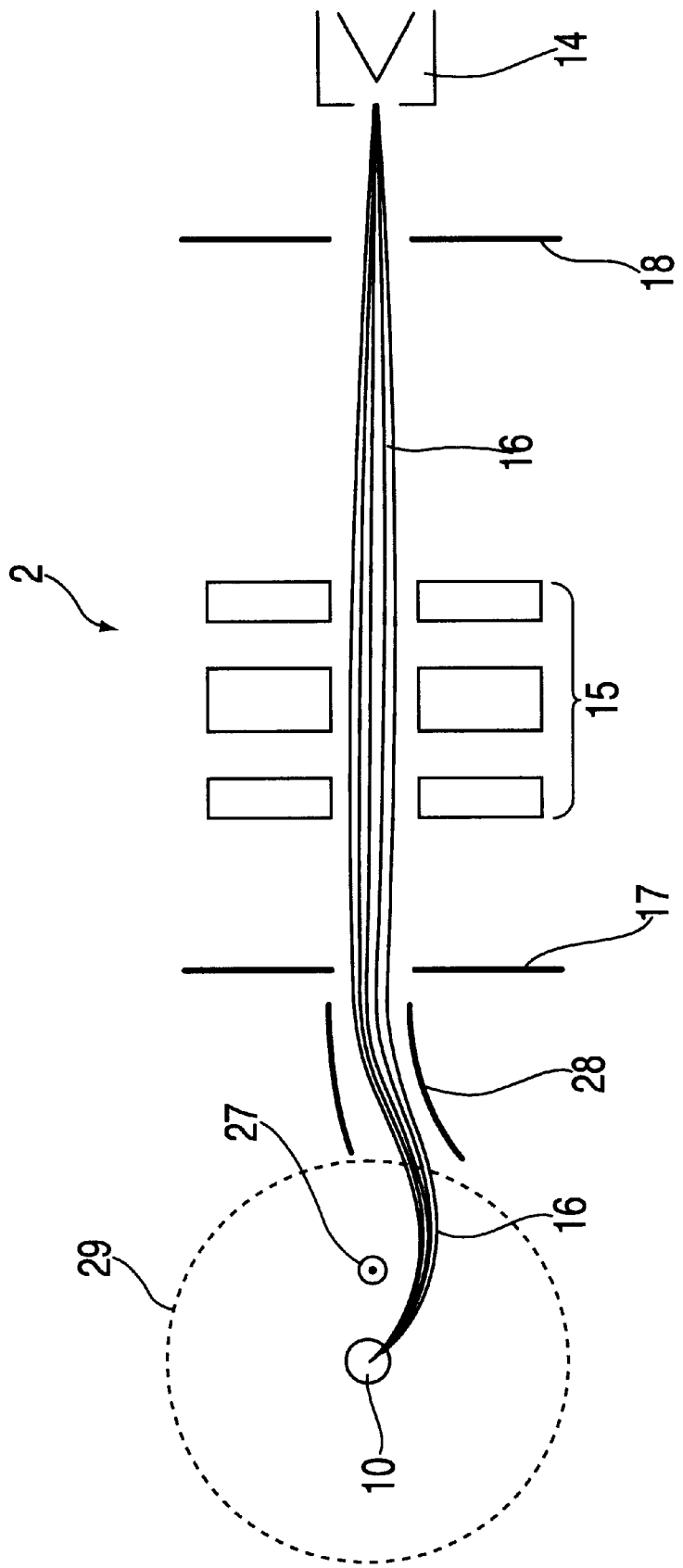
FIG. 5 shows a second path of an ion beam in accordance with the invention with the objective lens switched-on, FIG. 6 shows a third path of an ion beam in accordance with the invention with the objective lens switched-on, FIG. 7 shows double focusing in accordance with Mattauch and Herzog.

FIG. 5 shows a configuration alternate to that of FIG. 4 in which the ion beam 16 is initially directed radially onto the sample 10 but, prior to entrance into the magnetic field 27, is deflected by means of a pair of electrostatic deflection plates having curved deflection plates 28 in such a fashion that the ions are incident on the sample 10 along a curved path. The displacement of the ion beam 2 in accordance with FIG. 4 can also be combined with the electrostatic deflection in accordance with FIG. 5.

Figure 6:
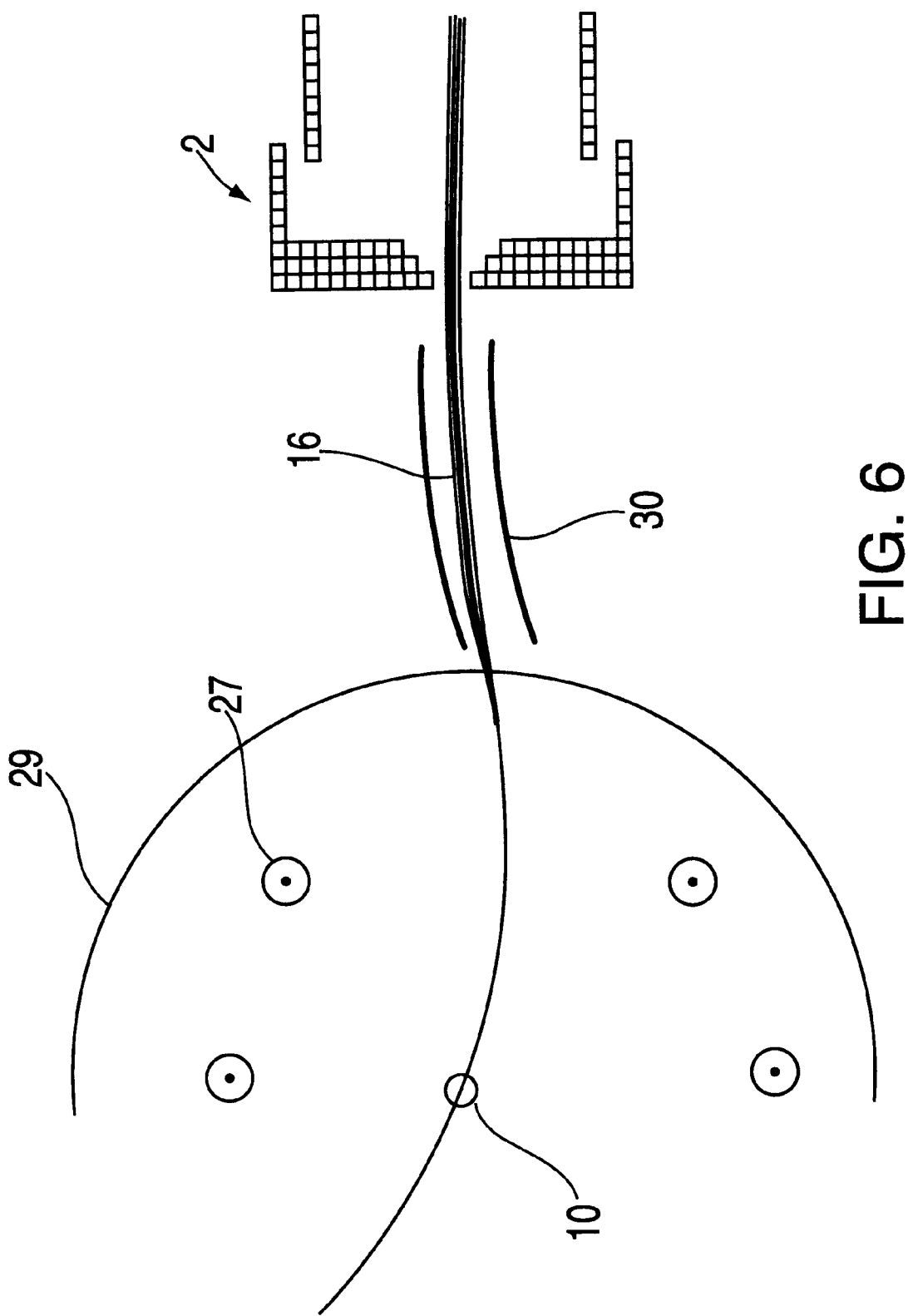

When the ion beam 16 has sufficient sharpness with respect to its energy and direction, it is possible, with the configurations in accordance with FIG. 4 and 5, to achieve a satisfactory focus on the sample 10. However the energy or directional dispersion in the magnetic field 27 increases with increasing energy defocusing or directional defocusing of the ion beam 16 leading to a fanning-out of the ion beam 16 at the sample location 26. In this case, double focusing (FIG. 6), is advantageous in order to compensate for the energy and directional dispersion. The ion-optic geometry and the field strength of the electric cylinder capacitor sector field 30 are thereby chosen in such a manner that, together with the geometry and the field strength of the magnetic sector field 27 of the objective lens 5, a double focusing condition is effected at the sample 10 (see also A. Benninghoven et. al Secondary Ion Mass Spectrometry, John Wiley & Sons, (1987)).

The initial ion beam 16 can thereby be directed radially or non-radially onto the sample 10. The deflection plates 28 form segments of a cylindrical capacitor 30. In this manner the ion beam 16 is not only guided along a curved path to be deflected onto the sample 10 under the influence of the magnetic field 27 but, by means of the double focussing of the cylindrical capacitor 30 in combination with the magnetic field 27, the energy and directional dispersion of the ion beam 16 is also compensated for to achieve a sharper focus on the sample 10.

Figure 7:
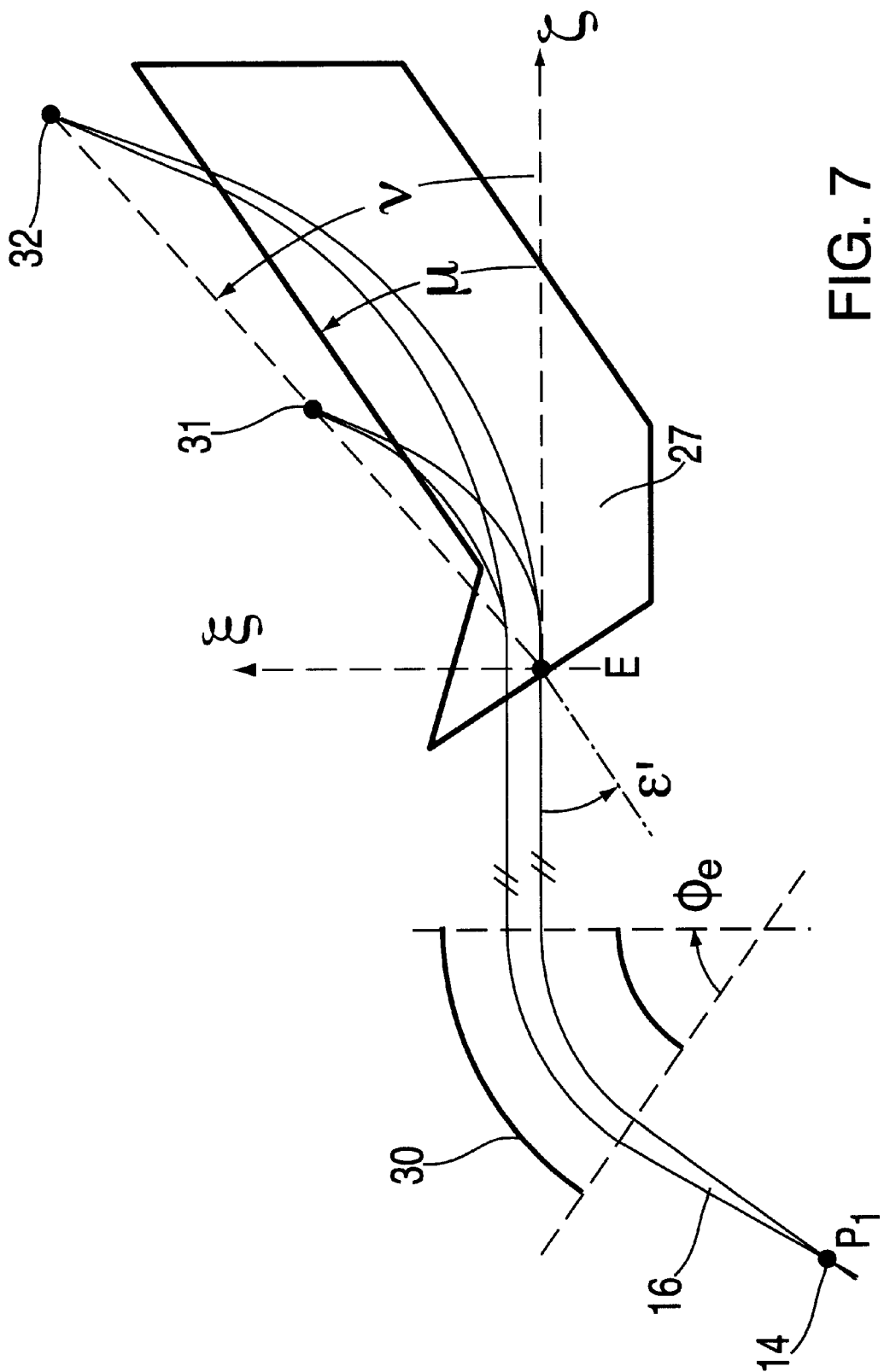

FIG. 7 shows a particular advantageous embodiment of double focusing which is referred to in the literature (see for example A. Benninghoven et al.) with regard to mass spectrometers as the configuration in accordance with Mattauch and Herzog. This is a special configuration with which the sector angle of the cylindrical capacitor 30 is 31.8° and the incident and exit angle of the ion beam 16 in the cylindrical capacitor is 90°. The ion path is shown for two differing ion masses initiating from a point P1 with energy and directional dispersion. One notices that, despite their energy and directional dispersion, ions of a first mass are focussed at a first focus 31 and ions with a second mass at a second focus 32. Of course, in the context of the invention, isotopes of differing masses are not used or at least substantially isotope-pure ion sources 14 so that the desired mass separation into two differing focuses 31, 32 needed in mass spectrometers is irrelevant. However, the compensation of the energy and directional dispersion can be advantageously utilized. With other magnetic field 27 configurations than the ones shown having a particular electrostatic field of a cylindrical capacitor 30, it is possible, as shown in the literature, to always select a cylindrical capacitor 30 which, in combination with the magnetic field 27, effects double focusing.

Figure 8:
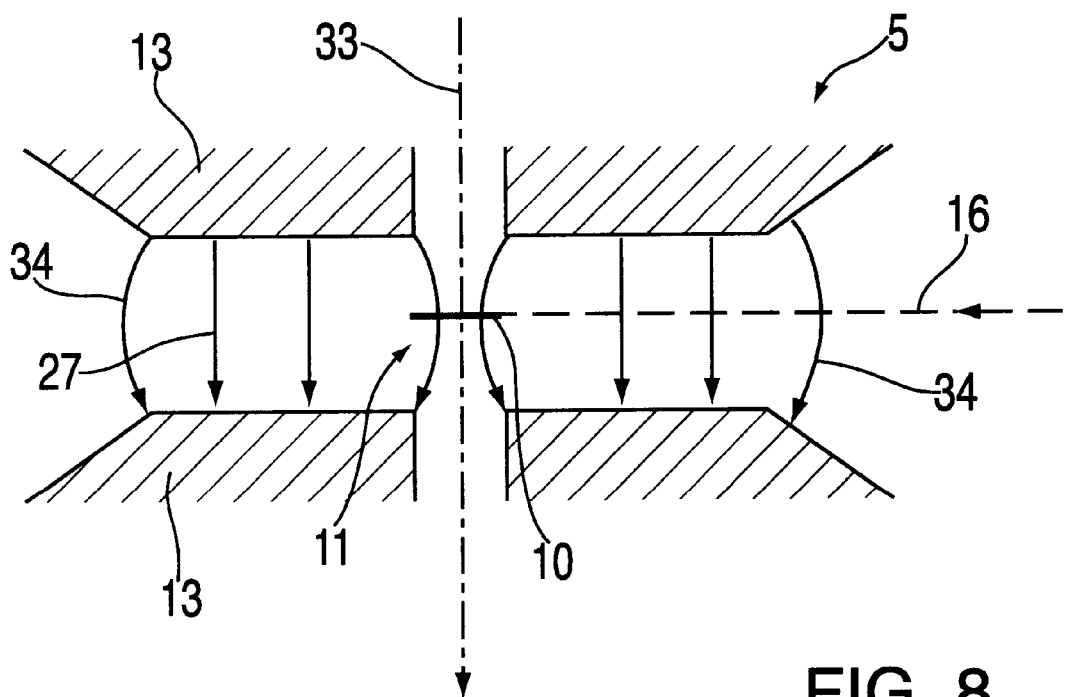
FIG. 8 shows a cut through a pole piece system of a converging single field objective lens with the magnetic field dependence and sample.

FIG. 8 shows a schematic sketch of a cut through the objective lens 5 or its pole pieces 13 of a transmission electron microscope 1. The lens is a condenser single field lens as utilized in prior art for effecting high resolution. Large magnification can be achieved by means of suitable projection lenses 6. However, for high-resolution, as strong a magnetic field as possible is desirable at the location of the sample 10 in particular more than 0.5 T and preferentially at least 1 to 2 T. A condenser single field objective lens is a lens with which the sample 10 is disposed between two pole pieces 13. A condenser single field lens is both a condenser and an imaging lens.

In order to be able to achieve a high magnetic field 27 at the location of the sample 10, the sample region 11 is very confined. The passage for the electron beam 13 has, depending on the type and resolution of the transmission electron microscope 1, a typical diameter of 0.5 to 1 cm and the separation with respect to the pole pieces 13 in the direction of the electron beam 33 is ca. 0.5 to 1 cm. The ion beam 16 advantageously travels, in the region of the objective lens 5, in the sample or objective plane 9 of the objective lens 5. It is, however, in principle also possible for the ion beam 16 to travel in a plane which is at an angle other than a right angle with respect to the electron beam 33. In this event, the increased influence of the fringe field 34 on the ion beam 16 must be taken into account or a theoretical or experimental determination of a suitable curved path as well as associated deflection plates 28 or the associated cylindrical capacitor 30 are required, thereby increasing complications.

Figure 9:
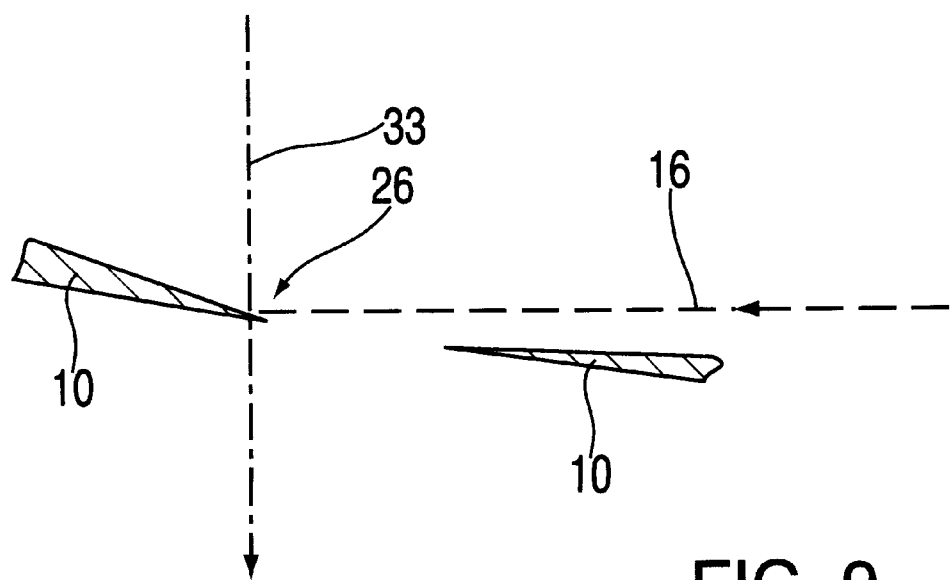
FIG. 9 shows a sketch of the locating of the sample in a sample region.

FIG. 9 shows a schematic configuration of the sample 10 during irradiation with an electron beam 33 and the ion beam 16. The sample 10 is held by a sample holder (not shown) preferentially in a goniometer suspension configured in such a fashion that the sample surface can be tilted at an angle between −10° to +10° with respect to the ion beam 16 under simultaneous ion thinning and transmission electron microscopic observation. The preceding treatment normally results in a hole of ca. 100 to 200 $\mu$m diameter in the sample 10. The edge of this hole is wedge-shaped and represents the usable sample region. Subsequent processing of the sample 10 to a desired sample thickness at a desired local sample location 26 can be carried out at the edge by means of grazing incidence of ion beam 16, wherein the sample location 26 can be simultaneously observed during ion thinning at high resolution with the electron beam 33.

List of Reference Symbols 1 transmission electron microscope
2 ion beam device
3 electron beam source 4 condenser lens
5 objective lens
6 projection lens
7 observation region
8 observation plane
9 objective plane
10 sample
11 sample region
12 first imaging plane
13 pole piece
14 ion source
15 ion lens
16 ion beam
17 collimator
18 additional collimator
19 voltage supply
20 scan generator
21 deflection amplifier
22 secondary electrons
23 secondary electron detector
24 ion scan image monitor
25 electron scan image monitor
26 sample location
27 magnetic field
28 deflection plates
29 pole piece edge
30 cylindrical capacitor
31 focus
32 focus
33 electron beam
34 fringe field

We claim:

1. An ion-etching device for ion thinning of a sample in a sample region of a transmission electron microscope having an objective lens and comprising an ion source for the production of an ion beam and an ion lens, a secondary electron detector for the production of an ion scan secondary electron image of the sample surface with the assistance of secondary electrons released by scanning ion irradiation and for positioning the ion beam via the ion scan secondary electron image onto a particular sample location, such that when the objective lens is switched-on the sample location can be observed simultaneously with the ion scan secondary electron image and with the electron beam of the transmission electron microscope in transmission wherein the ion energy is less than 5 keV and the ion beam in the vicinity of the objective lens travels in the objective plane of the objective lens and wherein, by taking into consideration the deflection of the ions of the magnetic field of the objective lens, the introduction of the ion beam into a magnetic sector field of the objective lens through which the ions pass is chosen in such a fashion that for the compensation of the influence of the magnetic field of the objective lens the magnetic sector field through which the ions pass deflects the ions along a curved path onto the particular sample location in a defined manner.

2. The ion-etching device according to claim 1, wherein an ion focus can be adjusted at the particular sample location by the ion lens and the ion focus at the particular sample location has a diameter between 0.5 and 100 µm.

3. The ion-etching device according to claim 1, further comprising deflection plates of an electrostatic cylindrical capacitor sector field which are configured, in combination with a magnetic sector field of the objective lens through which the ions pass, to effect a double focusing of the ions with regard to energy and initial direction.

4. A transmission electron microscope having an objective lens and an ion-etching device for ion thinning of a sample comprising an ion source for the production of an ion beam and an ion lens, a secondary electron detector for the production of an ion scan secondary electron image of the sample surface with the assistance of secondary electrons released by scanning ion irradiation and for positioning the ion beam via the ion scan secondary electron image onto a particular sample location, such that when the objective lens is switched-on the sample location can be observed simultaneously with the ion scan secondary electron image and with the electron beam of the transmission electron microscope in transmission, wherein the ion energy is less than 5 keV and the ion beam in the vicinity of the objective lens travels in the objective plane of the objective lens and wherein by taking into consideration the deflection of the ions in the magnetic field of the objective lens, the introduction of the ion beam into a magnetic sector field of the objective lens through which the ions pass is chosen in such a fashion that for the compensation of the influence of the magnetic field of the objective lens, the magnetic sector field through which the ions pass deflects the ions along a curved path onto the particular sample location in a defined manner.

5. The transmission electron microscope according to claim 4, wherein an ion focus can be adjusted at the particular sample location by the ion lens and the ion focus at the particular sample location has a diameter between 0.5 and 100 µm.

6. The transmission electron microscope according to claim 5, further comprising a sample holder for holding a sample surface, during simultaneous ion thinning and transmission electron microscopic observation, at an angle of −10° to +10° relative to the ion beam.

7. The transmission electron microscope according to claim 4, further comprising deflection plates of an electrostatic cylindrical capacitor sector field which are configured, in combination with a magnetic sector field of the objective lens through which the ions pass, to effect a double focusing of the ions with regard to energy and initial direction.

8. The transmission electron microscope according to claim 4, having an objective lens comprising a condenser single field lens.

9. The transmission electron microscope according to claim 4, wherein the magnetic sector field at the sample location is greater than 0.5 T.

10. The transmission electron microscope according to claim 4, wherein the energy of the electrons for production of the transmission electron image is greater than 100 keV.

11. The transmission electron microscope according to claim 4, adapted for high resolution transmission electron microscopy having a transverse resolution better than 1.5 nm during a simultaneous ion thinning.

12. A method for ion thinning of a sample in a sample region of a transmission electron microscope having an objective lens comprising the steps of: producing an ion beam with an ion source; producing a scanning electron secondary electron image of the sample surface with the assistance of the secondary electrons released during a scanned ion irradiation; positioning the electron beam via the ion scanned secondary electron image onto a particular sample location such that when the objective lens is switched-on, the sample location is observed in transmission with the electron beam of the transmission electron microscope simultaneously with the ion scan secondary electron image; wherein the ion beam travels in the region of the objective lens in the objective plane of the objective lens and wherein the ions of the ion beam enter into a magnetic sector field of the objective lens with an energy of less than 5 keV and wherein by taking into consideration the deflection of the ions in the magnetic field of the objective lens the ions are introduced into the magnetic sector field of the objective lens in such a fashion that for the compensation of the influence of the magnetic field of the objective lens the magnetic sector field through which the ions pass deflects the ions along a curved path onto the particular sample location in a defined manner.

13. The method according to claim 12, wherein an ion focus at the sample location is produced by the ion lens.

14. The method claim 12, wherein the ions travel through an electrostatic cylindrical capacitor sector field which is configured, in combination with the magnetic sector field of the objective lens through which the ions pass, to effect a double focusing of the ions with regard to energy and initial direction.

* * * * *